United States Patent
Asmus

(10) Patent No.: US 7,651,990 B2
(45) Date of Patent: Jan. 26, 2010

(54) FOAMABLE ALCOHOL COMPOSITIONS COMPRISING ALCOHOL AND A SILICONE SURFACTANT, SYSTEMS AND METHODS OF USE

(75) Inventor: Robert A. Asmus, Hudson, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 11/151,563

(22) Filed: Jun. 13, 2005

(65) Prior Publication Data

US 2006/0281663 A1 Dec. 14, 2006

(51) Int. Cl.
*C11D 3/48* (2006.01)
*C11D 9/36* (2006.01)

(52) U.S. Cl. ............ 510/138; 510/119; 510/122; 510/130; 510/135; 510/136; 510/466; 510/473; 510/475; 510/382; 510/384; 510/388

(58) Field of Classification Search ............ 510/119, 510/122, 130, 135, 136, 138, 466, 473, 475, 510/382, 384, 388
See application file for complete search history.

(56) References Cited

U.S. PATENT DOCUMENTS

| | | | |
|---|---|---|---|
| 2,054,989 A | 9/1936 | Moore | |
| 3,131,152 A | 4/1964 | Klausner | |
| 3,131,153 A | 4/1964 | Klausner | |
| 3,395,214 A | 7/1968 | Mummert | |
| 3,709,437 A | 1/1973 | Wright | |
| 3,770,648 A | 11/1973 | Mackles | |
| 3,824,303 A | 7/1974 | Lanzet | |
| 3,928,558 A * | 12/1975 | Cheesman et al. ............ 424/47 | |
| 3,962,150 A | 6/1976 | Viola | |
| 4,018,364 A | 4/1977 | Wright | |
| 4,311,695 A * | 1/1982 | Starch ............ 514/63 | |
| 4,440,653 A | 4/1984 | Briscoe et al. | |
| 4,478,853 A | 10/1984 | Chaussee | |
| 4,511,486 A | 4/1985 | Shah | |
| 4,559,226 A | 12/1985 | Fogel et al. | |
| 4,567,038 A * | 1/1986 | Ciaudelli et al. ............ 424/59 | |
| 4,613,592 A | 9/1986 | Benzoni | |
| 4,772,592 A | 9/1988 | Benzoni | |
| 4,826,828 A * | 5/1989 | Wilmott et al. ............ 514/63 | |
| 4,839,166 A | 6/1989 | Grollier et al. | |
| 4,839,167 A | 6/1989 | Yamamoto et al. | |
| 4,857,302 A * | 8/1989 | Decker et al. ............ 424/47 | |
| 4,897,262 A * | 1/1990 | Nandagiri et al. ............ 424/70.12 | |
| 4,906,459 A * | 3/1990 | Cobb et al. ............ 424/70.12 | |
| 4,915,934 A | 4/1990 | Tomlinson | |
| 4,956,170 A | 9/1990 | Lee | |
| 4,956,173 A * | 9/1990 | Le Fur et al. ............ 424/63 | |
| 4,981,678 A | 1/1991 | Tomlinson | |
| 4,983,377 A * | 1/1991 | Murphy et al. ............ 424/47 | |
| 4,986,922 A | 1/1991 | Snow et al. | |
| 5,100,658 A | 3/1992 | Bolich, Jr. et al. | |
| 5,104,646 A | 4/1992 | Bolich, Jr. et al. | |
| 5,128,123 A | 7/1992 | Brewster et al. ............ 424/65 | |
| 5,167,950 A | 12/1992 | Lins | |
| 5,180,584 A | 1/1993 | Sebag et al. | |
| 5,204,099 A * | 4/1993 | Barbier et al. ............ 424/401 | |
| 5,232,691 A | 8/1993 | Lemole | |
| 5,288,486 A | 2/1994 | White | |
| 5,290,555 A * | 3/1994 | Guthauser et al. ............ 424/401 | |
| 5,300,284 A * | 4/1994 | Wiechers et al. ............ 514/23 | |
| 5,314,684 A * | 5/1994 | Horoschak et al. ............ 424/70.12 | |
| 5,352,437 A | 10/1994 | Nakagawa et al. | |
| 5,362,484 A | 11/1994 | Wood et al. | |
| 5,484,597 A | 1/1996 | Slavtcheff et al. | |
| 5,494,533 A | 2/1996 | Woodin, Jr. et al. | |
| 5,547,662 A | 8/1996 | Khan et al. | |
| 5,549,888 A * | 8/1996 | Venkateswaran ............ 424/78.02 | |
| 5,567,428 A | 10/1996 | Hughes | |
| 5,612,324 A | 3/1997 | Guang Lin et al. | |
| 5,626,853 A | 5/1997 | Bara et al. | |
| 5,629,006 A * | 5/1997 | Hoang et al. ............ 424/405 | |
| 5,635,469 A | 6/1997 | Fowler et al. | |
| 5,662,893 A | 9/1997 | George et al. ............ 424/70 | |
| 5,665,332 A | 9/1997 | Mundschenk et al. | |
| 5,690,921 A * | 11/1997 | Lang et al. ............ 424/70.13 | |
| 5,693,255 A | 12/1997 | Okamoto et al. ............ 252/312 | |
| 5,733,535 A * | 3/1998 | Hollingshead et al. ............ 424/65 | |
| 5,756,077 A | 5/1998 | Syed et al. | |
| 5,767,161 A | 6/1998 | Stroppolo et al. | |
| 5,776,430 A | 7/1998 | Osborne et al. | |

(Continued)

FOREIGN PATENT DOCUMENTS

CA 2534692 2/2005

(Continued)

OTHER PUBLICATIONS

Amendment and Response filed Oct. 31, 2007 in U.S. Appl. No. 11/340,778 (22 pgs).

(Continued)

*Primary Examiner*—Charles I Boyer

(57) ABSTRACT

A composition, systems for dispensing the composition and methods for the use of the composition are described. The composition comprises:
(A) Monohydric alcohol in an amount sufficient to provide antimicrobial activity;
(B) Surfactant comprising a dimethicone surfactant; and
(C) Builder, the builder in an amount sufficient to provide stability or to improve the stability of a foam formed from the composition.

31 Claims, No Drawings

U.S. PATENT DOCUMENTS

| | | | | |
|---|---|---|---|---|
| 5,824,320 | A * | 10/1998 | Rouillard et al. | 424/401 |
| 5,856,347 | A * | 1/1999 | Hashiguchi et al. | 514/370 |
| 5,908,619 | A | 6/1999 | Scholz | 424/78 |
| 5,919,439 | A | 7/1999 | Torgerson et al. | |
| 5,928,993 | A | 7/1999 | Johansson | |
| 5,935,587 | A | 8/1999 | Cauwet et al. | |
| 5,951,993 | A | 9/1999 | Scholz et al. | |
| 5,955,408 | A | 9/1999 | Kaiser et al. | |
| 5,972,356 | A * | 10/1999 | Peffly et al. | 424/401 |
| 5,980,876 | A | 11/1999 | Peffly | |
| 6,019,997 | A | 2/2000 | Scholz et al. | 424/449 |
| 6,086,856 | A | 7/2000 | Saferstein et al. | |
| 6,090,395 | A | 7/2000 | Asmus et al. | |
| 6,117,440 | A * | 9/2000 | Suh et al. | 424/407 |
| 6,183,766 | B1 * | 2/2001 | Sine et al. | 424/405 |
| 6,255,265 | B1 | 7/2001 | Van Gunst et al. | |
| 6,262,128 | B1 | 7/2001 | Stern et al. | |
| 6,333,039 | B1 | 12/2001 | Fendler et al. | |
| 6,342,470 | B1 | 1/2002 | Aronson et al. | |
| 6,352,701 | B1 | 3/2002 | Scholz et al. | |
| 6,383,997 | B1 | 5/2002 | McManus | |
| 6,410,005 | B1 | 6/2002 | Galleguillos et al. | |
| 6,423,329 | B1 * | 7/2002 | Sine et al. | 424/405 |
| 6,472,356 | B2 | 10/2002 | Narula et al. | |
| 6,491,840 | B1 | 12/2002 | Frankenbach et al. | |
| 6,497,864 | B1 | 12/2002 | Samain et al. | |
| 6,524,494 | B2 | 2/2003 | Hart et al. | |
| 6,524,594 | B1 | 2/2003 | Santora et al. | |
| 6,528,544 | B2 | 3/2003 | Stern et al. | |
| 6,534,069 | B1 | 3/2003 | Asmus et al. | |
| 6,537,952 | B2 | 3/2003 | Hayward et al. | |
| 6,562,360 | B2 | 5/2003 | Scholz et al. | |
| 6,582,711 | B1 * | 6/2003 | Asmus et al. | 424/405 |
| 6,610,315 | B2 | 8/2003 | Scholz et al. | |
| 6,617,294 | B2 | 9/2003 | Narula et al. | |
| 6,623,744 | B2 | 9/2003 | Asmus et al. | |
| 6,638,527 | B2 | 10/2003 | Gott et al. | |
| 6,641,825 | B2 | 11/2003 | Scholz et al. | |
| 6,685,952 | B1 | 2/2004 | Ma et al. | |
| 6,696,053 | B1 * | 2/2004 | Ma et al. | 424/70.27 |
| 6,730,621 | B2 | 5/2004 | Gott et al. | |
| 6,762,158 | B2 | 7/2004 | Lukenbach et al. | |
| 6,818,603 | B2 | 11/2004 | Aleles et al. | |
| 7,081,246 | B2 | 7/2006 | Asmus et al. | |
| 7,566,460 | B2 | 7/2009 | Asmus et al. | |
| 2002/0127253 | A1 | 9/2002 | Scholz et al. | |
| 2002/0142018 | A1 | 10/2002 | Scholz et al. | |
| 2002/0160029 | A1 | 10/2002 | Asmus et al. | |
| 2002/0160924 | A1 | 10/2002 | Bertrem et al. | |
| 2003/0211066 | A1 | 11/2003 | Scholz et al. | |
| 2003/0215418 | A1 | 11/2003 | Asmus et al. | |
| 2004/0071748 | A1 | 4/2004 | Asmus et al. | |
| 2004/0191195 | A1 * | 9/2004 | Collins et al. | 424/61 |
| 2004/0191274 | A1 | 9/2004 | Grayson | |
| 2004/0219227 | A1 * | 11/2004 | Modak et al. | 424/641 |
| 2004/0241099 | A1 | 12/2004 | Popp et al. | |
| 2004/0247685 | A1 * | 12/2004 | Modak et al. | 424/488 |
| 2004/0265240 | A1 | 12/2004 | Tamarkin et al. | |
| 2005/0003990 | A1 | 1/2005 | Smith et al. | |
| 2005/0129626 | A1 | 6/2005 | Koivisto et al. | |
| 2005/0222001 | A1 | 10/2005 | Baumeister et al. | |
| 2006/0018847 | A1 | 1/2006 | Kroepke et al. | |
| 2006/0110416 | A1 * | 5/2006 | Ryles et al. | 424/401 |
| 2006/0121071 | A1 | 6/2006 | Asmus et al. | |
| 2006/0182690 | A1 | 8/2006 | Veeger et al. | |
| 2006/0263396 | A1 | 11/2006 | Asmus et al. | |
| 2007/0148101 | A1 | 6/2007 | Snyder et al. | |
| 2008/0108704 | A1 | 5/2008 | Asmus et al. | |

FOREIGN PATENT DOCUMENTS

| | | |
|---|---|---|
| EP | 0 213 527 | 3/1987 |
| EP | 0 117 889 | 11/1987 |
| EP | 0 260 641 A2 | 3/1988 |
| EP | 0 689 767 | 1/1996 |
| EP | 0 990 412 | 4/2000 |
| EP | 1811013 | 7/2007 |
| JP | 61-500357 | 3/1986 |
| JP | 06279268 | 10/1994 |
| JP | 07285808 | 10/1995 |
| JP | 11349418 | 12/1999 |
| WO | WO 93/00089 | 1/1993 |
| WO | 95/01384 | 1/1995 |
| WO | WO 95/01384 | 1/1995 |
| WO | 95/03772 | 2/1995 |
| WO | 97/00667 | 1/1997 |
| WO | 97/00668 | 1/1997 |
| WO | WO 99/20250 | 4/1999 |
| WO | WO 00/06107 | 2/2000 |
| WO | WO 00/47183 | 8/2000 |
| WO | WO 03/034994 | 5/2003 |
| WO | WO 03/053388 | 7/2003 |
| WO | WO 2005/030917 | 4/2005 |
| WO | WO 2006/066888 | 6/2006 |
| WO | WO 2006/094387 | 9/2006 |

OTHER PUBLICATIONS

Amendment and Response filed Oct. 31, 2007 in U.S. Appl. No. 10/400,597 (39 pgs.).
U.S. Appl. No. 10/400,597, filed Mar. 27, 2003, Scholz et al.
U.S. Appl. No. 10/463,497, filed Jun. 17, 2003, Asmus et al.
U.S. Appl. No. 11/340,778, filed Jan. 26, 2006, Asmus et al.
U.S. Appl. No. 11/492,635, filed Jul. 25, 2006, Asmus et al.
U.S. Appl. No. 11/928,966, filed Oct. 30, 2007, Asmus.
Buhler, "Kollidon® Polyvinylpryrrolidone for the pharmaceutical industry," Product Information Manual, Mar. 1998, 4th Edition, 288 pgs. (particularly page 178).
Domsch, *Die kosmetischen Präparate* [Preparations in Cosmetics], vol. 11, 4th Edition, Verlag fur die chem., Industrie, 1992, p. 57 + p. 118, formulation RZ2.114.
Goddard et al., "Novel gelling structures based on polymer/surfactant systems," J. Soc. Cosmet. Chem., 1991;42:19-34.
Sivadasan and Somasurdaran, "Polymer- Surfactant Interactions and the Association Behavior of Hydrophobically Modified Hydroxyethylcellulose,"*Colloids and Surfaces*, 1990;49:229-239.
U.S. Appl. No. 12/552,126, filed on Sep. 1, 2009; and entitled "Formable Alcohol Compositions, Systems and Methods of Use".

* cited by examiner

FOAMABLE ALCOHOL COMPOSITIONS COMPRISING ALCOHOL AND A SILICONE SURFACTANT, SYSTEMS AND METHODS OF USE

The present invention relates to foamable alcohol compositions, systems for dispensing the compositions and methods for the use of the compositions.

BACKGROUND

Foamable soap products contain a significant quantity of air. While these compositions can be economically manufactured as compared with non-foamable compositions, the formulation of foamable compositions comprising a high alcohol content has generally required the compositions to be provided as aerosol products which include a propellant (e.g., hydrocarbon, fluorocarbon, compressed gas) to facilitate foaming when the composition is dispensed from an aerosol container. These aerosol compositions can also include polymeric gelling agents, moderately high molecular weight (e.g., $C_{16}$ to $C_{22}$) alcohols and nonionic surfactants, for example. Aerosol products are costly to manufacture because of the need for a pressurized container and the inclusion of a foaming propellant.

In the formulation of non-aerosol soap products having a high alcohol content, surfactants have been included in such compositions to facilitate some level of foaming when the compositions are dispensed through a mechanical pump or the like. Surfactants can facilitate at least some degree of initial foaming, but such non-aerosol foams are often unstable and tend to collapse as soon as they are dispensed. While some fluorochemical surfactants have been known to facilitate more stable foams in non-aerosol compositions, fluorochemical surfactants may raise environmental concerns.

There is a need to provide foamable alcohol-containing compositions that are formulated to be anti-microbial and which can be applied to the skin (e.g., the hands). There is a need for alcohol-containing compositions that will form a stable foam in the absence of an aerosol propellant and which will deliver alcohol to the skin for rapid skin disinfection.

Within the foregoing need, it is desirable to provide foamable, low viscosity, alcohol-containing compositions that are safe and efficacious while providing properties that may be desired by the consumer.

SUMMARY

In one aspect, the present invention provides a composition, comprising:
  (A) Monohydric alcohol in an amount sufficient to provide antimicrobial activity;
  (B) Surfactant comprising a dimethicone surfactant; and
  (C) Builder, the builder in an amount sufficient to provide stability or to improve the stability of a foam formed from the composition.

In another aspect, the invention provides a system comprising a container and the composition as described above, the composition contained within the container under pressure and a propellant present within the composition.

In still another aspect, the invention provides a system comprising a dispenser comprising a reservoir and a hand pump; and the composition as described above contained within the reservoir.

In still another aspect, the invention provides a skin sanitizer comprising the composition as described above.

In still another aspect, the invention provides a pre-surgical hand scrub comprising the composition as described above.

In still another aspect, the invention provides a method for sanitizing a surface, comprising applying a volume of the composition as described above to the surface, the composition being in the form of a stable foam.

It will be appreciated that the terms used herein will be understood as being defined according to the understanding of those skilled in the art at the time of the present invention. However, certain terms used herein shall be understood as having the meaning that is expressly set forth herein:

"Builder" refers to a material that can be incorporated as a component in the compositions of the invention to aid in the creation of a stable foam when the composition is dispensed from an aerosol or a non-aerosol dispenser. Compositions comprising a builder can produce lower foam densities (greater volume) as compared to the same volume of the composition in the absence of the builder.

"Emollient" as used herein refers broadly to materials which are capable of maintaining or improving the moisture level, compliance, or appearance of the skin.

"Foam" refers to a frothy mass of bubbles formed on or from a liquid (e.g., the compositions of the invention).

"HLB" means the "hydrophile-liphophile balance," or the balance between the oil soluble and water soluble moieties in a surface active molecule or surfactant.

"Polymer" as used herein refers to a natural or synthetic molecule having repetitive units and a number average molecular weight of at least 20,000.

As used herein, "poly(propylene oxide)" and "poly(ethylene oxide)" are intended to be synonymous with "polypropylene glycol" or "PPG" and "polyethylene glycol" or "PEG," respectively. Poly(propylene oxide) and poly(ethylene oxide) are also abbreviated herein as "PPO" and "PEO," respectively.

"Solvent", "solvent system" or "hydroalcoholic solvent" as used herein refer to the alcohol and water combination in the present invention.

"Stable," as used when referring to a foamed composition, refers to foam that maintains a measurable height for a period of time of at least about 5 seconds following creation of the foam (e.g., by shaking the composition or by dispensing the composition from an aerosol or non-aerosol dispenser at ambient temperature). The stability of a particular foam may further be expressed in terms of the height of the foam after a measured period of time (e.g., 6 mm after 1 minute). Foam height measurements are further discussed in the Examples.

Those skilled in the art will more fully understand the various features and aspect of the invention upon consideration of the remainder of the disclosure, including the Detailed Description, the Examples and the appended claims.

DETAILED DESCRIPTION

The invention provides a foamable composition comprised of alcohol, surfactant and builder. The compositions of the invention may be aqueous compositions. Optional ingredients such as antimicrobials and/or emollients, for example, may be included to provide or enhance the properties of the compositions. The compositions of the invention provide the benefits of a foam for the disinfection of skin by providing a composition with a sheer thinning viscosity that is better than that for gelled compositions and which can be more easily rubbed onto sensitive tissue. Additionally, the compositions of the invention generally will dry quicker than a gel following application to a surface such as the hands, for example.

Alcohol

The compositions of the invention will include at least one alcohol that provides the ability to rapidly kill a broad spectrum of microbes. The compositions of the invention are suitable for use on the skin or other surfaces and may be used as a disinfectant for the hands, for example. In embodiments of the invention, the alcohol or alcohols are monohydric alcohols. Typically, the compositions of the invention comprise alcohols having lower hydrocarbon chain lengths such as $C_2$ to $C_4$ alcohols. In some embodiments, the compositions of the invention comprise a single alcohol. In other embodiments, a blend of two or more alcohols may be present. In some embodiments, the alcohol will consist of ethanol. In still other embodiments, the alcohol will consist of propanol (e.g., n-propanol and/or isopropanol). In still other embodiments, the alcohol will consist of butanol (e.g., n-butanol, sec-butanol and tert-butanol). In some embodiments the alcohol is dissolved in water to provide an alcohol-water solvent.

Embodiments of the invention may comprise compositions having an alcohol content between about 35% and about 99.5% by weight. In some embodiments, the compositions of the invention will have an alcohol content within the range from about 60% to about 80%. Compositions having an alcohol content within the foregoing ranges typically provide an efficacious bacterial kill.

Surfactants

At least one surfactant is present in the compositions of the invention. In some embodiments, surfactant may be present in the compositions of the invention at concentration ranges from about 0.1% to about 10% by weight, based on the total weight of the composition. In some embodiments, the surfactant may be present in a composition at a concentration ranging from about 0.5% to about 5% by weight, based on the total weight of the composition. Those skilled in the art will appreciate that certain surfactants may impart a tacky or even a greasy feel to a composition when the surfactant concentration is greater than 5% by weight. While such surfactant concentrations are contemplated as within the scope of the invention, the skilled artisan may wish to consider the cosmetic effects of surfactant concentrations when formulating a composition for use by the consumer. In some embodiments, the compositions of the invention are formulated with non-fluorinated surfactants and without the need for fluorochemical propellants.

Specific surfactants useful in the invention include dimethicone surfactants. Examples of dimethicone surfactants include dimethicone copolyols—a polymer of dimethylsiloxane with polyoxyethylene (PEO) and/or polyoxypropylene (PPO) side chains. In some embodiments, these surfactants can be hydroxyl, methoxy or butoxy terminated, and the molar ratio of PEO to PPO (PEO/PPO) can range from 0/50 to 50/0 and the molecular weight of the dimethicone portion can range from 200 to 20,000. The surfactants used in the invention can comprise specific dimethicone surfactants. Specific surfactants suitable for use in embodiments of the invention include, without limitation, methoxy-terminated polyethylene glycol dimethicone having an average molecular weight of about 3000; dimethicone with a pendant ether of 35/65 (w/w) polyethylene glycol/polypropylene glycol copolymer having a combined average molecular weight of about 7,000; dimethicone copolyol with 18/18 (molar ratio) polyethylene glycol/polypropylene glycol; a dimethicone copolyol with 17/18 (molar ratio) polyethylene glycol/polypropylene glycol; a dimethicone copolyol with polyethylene glycol/polypropylene glycol-methoxy terminated having an average molecular weight of about 20,000 and a HLB of 9-12; dimethicone copolyol with a methoxy-terminated polyethylene glycol having a combined average molecular weight of about 3000; dimethicone copolyol with a methoxy-terminated polyethylene glycol having a combined average molecular weight of about 6000; dimethicone copolyol with a hydroxy terminated polyethylene glycol having a combined average molecular weight of about 5000 with an HLB of 13-17; dimethicone copolyol lactate; silicone copolyol pelargonate; hydroxyl-capped dimethicone copolyol; hydroxyl-terminated polyethylene glycol-12 dimethicone; dimethicone copolyol laurate; Silicone Quaternary 1; hydroxy-terminated polyethylene glycol dimethicone having an average molecular weight of about 4000; methoxy-terminated polyethylene glycol dimethicone having an average molecular weight of about 600; Silicone Quaternary 2 (Myristyl); sodium dimethicone copolyol acetyl methyltaurate; butoxy-terminated poly(propylene oxide)dimethicone having an average molecular weight of about 3,000; and silicone copolyol isostearate.

Additionally, the following surfactants may be useful in the invention: dimethicone bisamino hydroxypropyl copolyol, dimethicone copolyol acetate, dimethicone copolyol adipate, dimethocone copolyol almondate, dimethicone copolyolamine, dimethicone copolyol avocadoate, dimethicone copolyol beeswax, dimethicone copolyol behenate, dimethicone copolyol benzoate, dimethicone copolyol bishydroxy ethylamine, dimethicone copolyol borageate, dimethicone copolyol butyl ether, dimethicone copolyol cocoa butterate, dimethicone copolyol crosspolymer, dimethicone copolyol dhupa butterate, dimethicone copolyol ethyl ether, dimethicone copolyol hydroxy stearate, dimethicone copolyol isostearate, dimethicone copolyol kokum butterate, dimethicone copolyol lactate, dimethicone copolyol laurate, dimethicone copolyol mango butterate, dimethicone copolyol meadowfoamate, dimethicone copolyol methyl ether, dimethicone copolyol mohwa butterate, dimethicone copolyol octyldodecyl citrate, dimethicone copolyol olivate, dimethicone copolyol phosphate, dimethicone copolyol phthalate, dimethicone copolyol sal butterate, dimethicone copolyol shea butterate, dimethicone copolyol stearate, dimethicone copolyol undecylenate, dimethicone hydroxypropyl trimonium chloride, dimethicone propyl pg-betaine, polysilicone-10, polysilicone-8, dimethcone propylethylenediamine behenate, amino bispropyl dimethicone aminoethylaminopropyl dimethicone, behentrimonium dimethicone copolyol phthalate, bis-aminopropyl copolyol aminopropyl dimethicone, bis-hydroxyethoxypropyl dimethicone, cetyl triethylmonium dimethicone copolyol succinate, dimethicone copolyol sulfate, dimethicone copolyol phosphate, dimethicone polyglycerol, disodium copolyol dimethicone sulfosuccinate, copolyol polydimethylsiloxyethyl dimethicone, copolyol pg-coco-glucoside dimethicone, copolyol nonafluorohexyl dimethicone copolymer, copolyol methyl ether lauroxy peg amidopropyl dimethicone, copolyol oleyl ether dimethicone, sodium carboxydecyl copolyol dimethicone.

Combinations of two or more of the foregoing dimethicone surfactants in a single composition are also contemplated within the scope of the invention Builder At least one builder may be included in the compositions of the invention in order to stabilize the foams produced from the compositions when the compositions are shaken, or when they are dispensed from either an aerosol or a non-aerosol dispenser. In some embodiments, the inclusion of certain builders can provide cosmetic attributes to the compositions of the invention. Suitable builders can include one or more of the following: poly(ethylene oxide), hydroxyethyl cellulose, hydroxypropyl cellulose. In some embodiments, the builder will comprise only one of the foregoing. In other embodiments, the builder will comprise a combination of two or more of the foregoing builder. In some embodiments, the builder will comprise a poly(ethylene oxide) having an average molecular weight in the range from about 200,000 to about 4,000,000. One poly(ethylene oxide) suitable for use in the compositions of the invention is that know under the designation POLYOX™ and commercially available from Dow Chemical Canada Inc., Sarnia, Ontario. Suitable POLYOX compositions include those designated as "WSR N12K" having an average molecular weight of 1,000,000; "WSR-301" having an average molecular weight of 4,000,000; "WSR N60K" having an average molecular weight of 2,000,000; and "WSR N-80" having an average molecular weight of 200,000.

The builder, when included in the compositions of the invention, may be present at a concentrations between about 0.001% and about 5% by weight. In some embodiments, the builder may be present at concentrations less then or equal to about 0.1%. In some embodiments, the builder is present in the composition at concentrations of about 0.06%.

In general, the builder enhances the stability of the foam produced when the composition of the invention is shaken or when the composition is dispensed. Builders suitable for use in the invention will include those that provide or enhance the stability of the foam—i.e., those that provide a measurable foam height over at least about 5 seconds following the creation of the foam. In some embodiments, the builder is soluble in the alcohol that is used in the compositions of the invention. In some embodiments, the builder will be swellable within the alcohol. In still other embodiments, the builder can be characterized as dispersible in the alcohol.

In some embodiments, suitable foam builders include compounds comprising high molecular weight polymers. In some embodiments, these polymers are alcohol or hydroalcoholic soluble. Specific polymers useful in the invention include, without limitation: Poly(ethylene oxide) (molecular wt of 100,000 to 10,000,000), high molecular weight polyethylene-polypropylene copolymers, hydroxyethyl cellulose, hydroxypropyl cellulose. When present, the polymer will be at a concentration of between about 0.001 and about 5%. In some embodiments, the polymer concentration will be between about 0.01% and about 0.5%.

Polymers within the following classes can be useful as builders in the compositions of the invention: hydroxypropyl guar, polyquaternium-4, polyquaternium-10, cetyl hydroxyethylcellulose, ethylhydroxy ethyl cellulose, polyglycerol, high molecular wt. polyoxamer, high molecular wt. polyoxamine, polyacrylamide, high molecular wt polyethylene glycol esters and ethers with alkyl alcohols or acid functional alkyls, polyacrylamidomethylpropane sulfonic acid, polyacrylic acid, polyethylene/isopropyl maleate/malaic acid copolyol, polymethacrylamidopropyltrimonium chloride, polymethacrylamidopropyltrimonium methosulfate, polymethacrylic acid, polyquaternium-1 to polyquaternium-47, polyvinyl methyl ether, butylated poly vinyl pyrrolidone, hydroxypropyl methylcellulose; hydroxypropyl cellulose; crosslinked and noncrosslinked homopolymer or crosslinked and noncrosslinked copolymer containing n-vinyl lactam monomeric units.

Non-limiting examples of N-vinyl lactam monomers are N-vinyl-2-pyrrolidone; N-vinyl-2-valerolactam; N-vinyl-2-caprolactam; and mixtures of any of the foregoing. Typically, the poly(N-vinyl lactam) is a homopolymer of N-vinyl-2-pyrrolidone. Nonlimiting examples of comonomers useful with the aforementioned N-vinyl lactam monomers include N,N-dimethylacrylamide, acrylic acid, methacrylic acid, hydroxyethylmethacrylate, acrylamide, 2-acrylamido-2-methyl-1-propane sulfonic acid or its salt, and vinyl acetate.

While the foregoing builders can be added to the compositions of the invention individually, combinations of two or more such builders are also contemplated within the scope of the invention as well as derivatives thereof.

Viscosity of Compositions

The compositions of the invention will typically be of very low viscosities at 23° C. In some embodiments, the compositions of the invention can have different viscosities depending on the state of the composition. For example, a composition in a pre-dispensed condition, i.e., it is in a "pre-foamed" state in a dispenser prior to being dispensed, can have a viscosity within the range from about 0.5 to about 100 cps at 23° C. In some embodiments, the prefoam viscosities of compositions of the invention will range from about 0.5 cps to about 50 cps. In still other embodiments, the prefoam viscosities of compositions of the invention will range from about 0.5 cps to about 20 cps. When a composition of the invention is dispensed from a non-aerosol pump-type dispenser, the composition will foam, and the foam will typically be of a higher viscosity than the viscosity of the liquid "non-foamed" composition prior to dispensing. It will also be appreciated that the addition of an emollient and/or other optional ingredients (discussed herein) can also have an affect on viscosity (either positively or negatively).

Foam Density

The compositions of the invention will foam when shaken of dispensed from a dispenser. It will be appreciated that the foam densities of the compositions can vary depending on any of a variety of factors. For example, the viscosity of the unfoamed composition, discussed above, can have an effect on foam density. Moreover, the design of the dispenser or the non-aerosol pump used to deliver the foamed composition can have an effect on the foam density of the composition to the extent that the dispenser and/or the pump effect the foaming of the composition. Additionally, the amount of force applied to the pump and the relative speed at which the pump is operated when dispensing the composition can also have an effect on the foaming of the composition and its resulting viscosity.

Optional Ingredients

In addition to alcohol-water, surfactant and builder, the compositions of the present invention may optionally include other ingredients such as salts, emollients, stabilizers, antimicrobials, fragrances, therapeutic agents, propellants and additional emulsifiers. Each of these optional ingredients along with the effect each has upon the properties of the final composition is discussed below.

Emollients can optionally be added to the compositions of the invention so that the compositions can be provided in a form that is capable of increasing the moisture content of the stratum corneum when the composition is applied to a user's hands, for example. Emollients are generally separated into two broad classes based on their function. The first class of emollients function by forming an occlusive barrier to prevent water evaporation from the stratum corneum. The second class of emollients penetrate into the stratum corneum and physically bind water to prevent evaporation. The first class of emollients is subdivided into compounds which are waxes at room temperature and compounds which are liquid oils. The second class of emollients includes those which are water soluble and are often referred to as humectants.

As referred to herein, the alcohol-water, surfactant and builder components used in the compositions of the invention are separate and distinct from components identified as emollients and optionally added to the composition. Emollients may be added to the compositions in addition to the aforementioned silicone block surfactants and builder compounds which may also aid in maintaining or improving the skin condition of the user. In some embodiments, added emollients may be included the compositions of the invention at a concentration between about 0 and about 30% by weight. In some embodiments, the added emollient can be present in the composition at a concentration between about 0.5% and about 20%. In still other embodiments, the emollient concentration can be between about 1% and about 12% by weight. Suitable emollients may be selected from any of the classes known in the art. A general list of useful emollients appears, for example, in U.S. Pat. No. 4,478,853 and in EPO patent application 0 522 624A1 as well as in the CTFA Cosmetic Ingredient Handbook published by The Cosmetic, Toiletry, and Fragrance Association, Wash. D.C. (1992) under the listings "Skin Conditioning agents," "emollients," "humectants," "miscellaneous" and "occlusive."

In some embodiments, suitable emollients may be chosen from the following nonlimiting list of general emollients, occlusive emollients and humectants. Examples of general emollients include short chain alkyl or aryl esters ($C_1$-$C_6$) of long chain straight or branched chain alkyl or alkenyl alcohols or acids ($C_8$-$C_{32}$) and their polyethoxylated derivatives; short chain alkyl or aryl ester ($C_1$-$C_6$) of $C_4$-$C_{12}$ diacids or diols optionally substituted in available positions by —OH; alkyl or aryl $C_1$-$C_{10}$ esters of glycerol, pentaerythritol, ethylene glycol, propylene glycol, as well as polyethoxylated derivatives of these and polyethylene glycol; $C_{12}$-$C_{22}$ alkyl esters or ethers of polypropylene; $C_{12}$-$C_{22}$ alkyl esters or ethers of polypropylene/polyethylene glycol copolymer.

Examples of occlusive emollients include cyclic and linear dimethicones; polydialkylsiloxanes; polyaryialkylsiloxanes; long chain ($C_8$-$C_{36}$)alkyl and alkenyl esters of long straight or branched chain alkyl or alkenyl alcohols or acids; long chain ($C_8$-$C_{36}$)alkyl and alkenyl amides of long straight or branched chain ($C_8$-$C_{36}$)alkyl or alkenyl amines or acids; hydrocarbons including straight and branched chain alkanes and alkenes such as squalene, squalane and mineral oil; jojoba oil; polysiloxane polyalkylene copolymers; short chain alkyl or aryl esters ($C_1$-$C_{36}$) of $C_{12}$-$C_{22}$ diacids or diols optionally substituted in available positions by OH such as diisopropyl dimer dilinoleate; and $C_{12}$-$C_{22}$ alkyl and alkenyl alcohols; long chain alkyl or aryl esters ($C_8$-$C_{36}$) of $C_{12}$-$C_{22}$ diacides or diols optionally substituted in available positions by —OH, such as diisostearyl dimer dilinoleate; lanolin and lanolin derivatives; and beeswax and its derivatives.

Non-limiting examples of preferred humectant type emollients include glycerol, polyglycerols (including: diglycerol, triglycerol, polyglycerin-3, tetraglycerol, hexaglycerol, decaglycerols) propylene glycol, dipropylene glycol, polypropylene glycol, polyethylene glycol (PEG-2 to PEG-45M, preferably a molecular weight between about 300 and 1,000), sorbitol, polyhydric alcohol ethoxylates (e.g. sorbeth-6, sorbeth-30, glycereth-1 to glycereth-31) methoxides of polyethylene glycol (Methoxy PEG-2 to Methoxy PEG-100) methoxides of polyhydric alcohol ethoxylates (e.g. glycereth-7 methoxide), pantothenol, gluconic acid salts and the like. Other humectant-type agents like that could also be employed include: 1,2,6-hexanetriol, acetamide mea, aluminum hydroxide, arginine pea, butoxypropanol, butylene glycol, dimethyl imidazolidinone, dimethylsilanol hyaluronate, dipotassium glycyrrhizate, erythritol, ethoxy-diglycol, fructose, glucamine, gluconic acid, glucose, glucose glutamate, glucuronic acid, glutamic acid, glycogen, glycyrrhizic acid, heilmoor clay, hexacosyl glycol, histidine, hyaluronic acid, hydrogenated honey, hydrogenated starch, hydrolysate, hydrolyzed collagen, hydrolyzed elastin, hydrolyzed glycosaminoglycans, hydrolyzed keratin, hydrolyzed silk, hydrolyzed soy protein, hydrolyzed wheat protein, hydroxyethyl sorbitol, inositol, inositol hexa-pea, lactamide mea, lactic acid, lactitol, lactose, lysine pea, magnesium pea, maltitol, manganese pea, mannitol, mel (honey extract), menthyl pea, methyl gluceth-10, methyl gluceth-20, pea (pidolic acid), lactamide, polydextrose, polyglucuronic acid, polyglyceryl sorbitol, potassium pea, ppg-20 methyl glucose ether, ppg-38-buteth-37, saccharide isomerate, serica, silk amino acids, sodium carboxymethyl chitin, sodium lactate, sodium mannuronate methylsilanol, sodium pea, sodium pea methylsilanol, sodium polyglutamate, soluble collagen, sorbitol, sucrose, tea-lactate, tea-pea, trehalose, trilactin, urea, xylitol, *zea mays*, zinc pea, and combinations thereof.

The addition of one or more emollients may affect the viscosity and stability of the compositions of the present invention. In some embodiments, a single emollient may be added to the composition. In some embodiments, two or more emollients may be added to the composition. While any of a variety of emollients may be added to the formulations of the present invention, some embodiments will include wax and oil type emollients either alone or combined with water soluble emollients. In some embodiments of the invention, emollient systems can be comprised of humectants in addition to occlusive wax and oil emollients in concentrations that achieve a moisturizing effect and which maintains and improves the condition of the skin upon repeated use. Emollients may be non-comedogenic and chosen to avoid skin irritation or sensitization reactions.

In addition to the antimicrobial effects attributable to the presence of alcohol in the compositions of the present invention, one or more other antimicrobial agents ("secondary antimicrobial agents") may be added to enhance the antimicrobial properties of the compositions when they are used as pre-surgical hand scrubs or pre-surgical patient skin scrub replacements, for example. In other words, the foamed composition of the present invention can deliver a secondary antimicrobial agent to the skin. In some embodiments, the secondary antimicrobial agent is added in levels up to 10% by weight of the total composition. In some embodiments, it may be desirable to incorporate a secondary antimicrobial agent in the compositions of the invention to provide continued antimicrobial resistance to the growth or regrowth of the microorganisms following evaporation of the alcohol.

Non-limiting examples of suitable secondary antimicrobial agents include parachlorometaxylenol; triclosan; chlorhexidine and its salts such as chlorhexidine gluconate, poly hexamethylene biguanide and its salts such as poly hexamethylene biguanidine chloride, iodine, idodophors; fatty acid monoesters; poly-n-vinyl pyrrolidone-iodophors; silver oxide, silver and its salts, peroxides (e.g. hydrogen peroxide), antibiotics (e.g. neomycin, bacitracin, and polymixin B).

Additionally, other suitable ingredients can be used in the compositions of the invention to suppress the regrowth or possibly treat an infection of microorganisms, such as: 2,2-thiobis(4-chlorophenol); 4,4-isopropylidenediphenol; 5-amino-6-chloro-o-cresol; acetaminosalol; alcloxa; aldioxa; aluminum acetate; aluminum benzoate; aluminum diacetate; aluminum formate; aluminum phenolsulfonate; ammonium iodide; ammonium phenolsulfonate; benzisothiazolinone; benzotriazole; benzoxiquine; benzylparaben; berberine chloride; boric acid; cetethyl morpholinium ethosulfate; cetethyldimonium bromide; cetrimonium tosylate; cetylpyridinium chloride; chloramine-t; chlorothymol; cloflucarban; cocotrimonium chloride; colloidal sulfur; copper usnate; dedmhydantoin; dedmhydantoin dilaurate; dequalinium acetate; dequalinium chloride; dibromopropamidine diisethionate; dichloro-m-xylenol; dichlorophene; dichlorophenyl imidazoldioxolan; diiodomethyltolylsulfone; dimethyl hydroxymethylpyrazole; dimethylaminostyryl heptyl methyl thiazolium iodide; dodecylbenzyltrimonium chloride; domiphen bromide; ferulic acid; fluorosalan; glyoxal; hydroxymethyl dioxoazabicyclooctane; hydroxypropyl bistrimonium diiodide; ichthammol; isodecylparaben; isopropyl sorbate; lapyrium chloride; laurtrimonium trichlorophenoxide; lauryl isoquinolinium bromide; lauryl isoquinolinium saccharinate; laurylpyridinium chloride; m-cresol; mandelic acid; MDM hydantoin; MEAa-iodine; melaleuca alternifolia; methylbenzethonium chloride; mixed cresols; nonoxynol-12 iodine; nonoxynol-9 iodine; o-cresol; oxyquinoline benzoate; oxyquinoline sulfate; p-chlorophenol; p-cresol; PEG15 dedm hydantoin; PEG-15 dedm hydantoin stearate; PEG-5 dedm hydantoin; PEG-5 dedm hydantoin oleate; phenol; phenoxyethylparaben; phenyl salicylate; polymethoxy bicyclic oxazolidine; potassium iodide; potassium lactate; potassium phenoxide; potassium troclosene; quartronium-14; quaternium-24; quaternium-8; ricinoleamidopropyltrimonium methosulfate; sodium iodide; sodium p-chloro-m-cresol; sodium phenolsulfonate; sodium phenoxide; sodium usnate; steapyrium chloride; strontium peroxide; tea-sorbate; tetrabutyl ammonium bromide; thiabendazole; triacetin; undecylenamide dea; undecylenamide mea; undecylenamidopropyltrimonium methosulfate; undecyleneth-6; undecylenoyl peg-5 paraben; usnic acid; zinc acetate; zinc borate; zinc phenolsulfonate; zinc sulfate; zinc undecylenate; and combinations of the foregoing.

The following actives could also be of use to also reduce regrowth of microorganisms on skin: 2-bromo-2-nitropropane-1,3-dial; 4-hydroxybenzoic acid; 5-bromo-5-nitro-1,3-dioxane; 7-ethylbicyclooxazolidine; ammonium benzoate; ammonium bisulfite; ammonium propionate; ammonium sulfite; behentrimonium chloride; benzalkonium bromide; benzalkonium chloride; benzalkonium saccharinate; benzethonium chloride; benzoic acid; benzyl alcohol; benzylhemiformal; bromochlorophene; butyl benzoate; butylparaben; calcium benzoate; calcium paraben; calcium propionate; calcium salicylate; calcium sorbate; calcium undecylenate; cetalkonium chloride; cetearalkonium bromide; cetrimonium bromide; cetrimonium chloride; chloroacetamide; chlorobutanol; chlorophene; chloroxylenol; chlorphenesin; climbazole; dehydroacetic acid; diazolidinyl urea; dibromohexamidine isethionate; dichlorobenzyl alcohol; dimethyl oxazolidine; DMDM hydantoin; ethyl benzoate; ethylparaben; formaldehyde; formic acid; glutaral; hexamidine; hexamidine diisethionate; hexamidine paraben; hexetidine; hydrogenated tallowtrimonium chloride; imidazolidinyl urea; iodopropynyl butylcarbamate; isobutyl benzoate; isobutylparaben; isopropyl benzoate; isopropyl cresols; isopropylparaben; lauralkonium bromide; lauralkonium chloride; laurtrimonium bromide; laurtrimonium chloride; magnesium benzoate; magnesium propionate; magnesium salicylate; MEA o-phenylphenate; MEA-benzoate; MEA-salicylate; MEA-undecylenate; methenamine; methyl benzoate; methylchloroisothiazolinone; methyldibromo glutaronitrile; methylisothiazolinone; methylparaben; myristalkonium chloride; myristalkonium saccharinate; myrtrimonium bromide; o-cymen-5-01; o-phenylphenol; olealkonium chloride; p-chloro-m-cresol; phenoxyethanol; phenoxyisopropanol; phenyl benzoate; phenyl mercuric acetate; phenyl mercuric benzoate; phenyl mercuric borate; phenyl mercuric bromide; phenyl mercuric chloride; phenylparaben; piroctone olamine; polyaminopropyl biguanide; potassium benzoate; potassium butylparaben; potassium ethylparaben; potassium metabisulfite; potassium methylparaben; potassium o-phenylphenate; potassium paraben; potassium propionate; potassium propylparaben; potassium salicylate; potassium sorbate; potassium sulfite; propionic acid; propyl benzoate; propylparaben; quaternium-15; salicylic acid; sodium benzoate; sodium bisulfite; sodium butylparaben; sodium dehydroacetate; sodium ethylparaben; sodium formate; sodium hydroxymethylglycinate; sodium iodate; sodium metabisulfite; sodium methylparaben; sodium o-phenylphenate; sodium paraben; sodium propionate; sodium propylparaben; sodium salicylate; sodium sorbate; sodium sulfite; sodium undecylenate; sorbic acid; soytrimonium chloride; stearalkonium chloride; steartrimonium chloride; tallowalkonium chloride; tallowtrimonium chloride; thimerosal; triclocarban; triclosan; undecylenic acid; zinc pyrithione.

The present invention further encompasses embodiments incorporating antimicrobials such as benzoyl peroxide so that the composition may be useful as an acne medication, for example. In some embodiments, the compositions of the present invention may also be formulated with barrier compounds to form barrier creams and lotions. Materials which may be added to provide barrier protection for use as skin barriers to protect against diaper rash include but are not limited to 0.1 to 60% aldioxa, allantoin, aluminum acetate, aluminum hydroxide, bismuth subnitrate, boric acid, calamine, cellulose (microporous), cholecalciferol, cocoa butter, cod liver oil (in combination), colloidal oatmeal, cysteine hydrochloride, dexpanthenol, dimethicone, glycerin kaolin, lanolin (in combination), live yeast cell derivative, mineral oil, peruvian balsam, peruvian balsam oil, pertrolatum, protein hydrolysate (1-leucine, 1-isoleucine, 1-methionine, 1-phenylalanine, and 1-tyrosine), racemethionine, shark liver oil, sodium bicarbonate, sulfur, talc, tannic acid, topical starch, vitamin A, white petrolatum, zinc acetate, zinc carbonate and zinc oxide.

In some embodiments, the compositions of the invention may comprise one or more formulations containing antifungal agents for the treatment of fungal infections of the skin such as athlete's foot and the like.

While some embodiments will include one additional secondary antimicrobial agent, other embodiments of the invention can include two or more additional secondary antimicrobials. While the foregoing secondary antimicrobials can be added to the compositions individually or singly, combinations of two or more of the foregoing secondary antimicrobials are also contemplated within the scope of the invention.

In some embodiments, the compositions of the present invention may be formulated into non-aerosol products that can be dispensed from a reservoir using a hand-pump, for example, to dispense an amount of the composition whenever the hand pump is actuated. The amount of the composition dispensed by the pump may or may not be metered so that the amount of composition dispensed may or may not be consistent. Moreover, the compositions of the invention are not limited to being dispensed from only one type of dispenser or through only one type of hand pump.

In some embodiments, the compositions are capable of being formulated into an aerosol foam or a mousse by addition of propellant to the composition. Suitable propellants can be chosen from chlorofluorocarbons (CFCs), hydrochlorofluorocarbons (HCFCs), hydrofluorocarbons (HFCs), perfluorinated alkanes, and lower alkanes (C1-C5) as well as nitrous oxide dimethyl ether and other solvent-soluble propellants. Suitable lower alkanes include propane, butane, and isobutane, for example. In some embodiments, the propellant can comprise a 70/30 mixture of propane/isobutane. In order to produce an aerosol composition the composition is first formulated and charged into an appropriate pressure rated container. A suitable propellant may then be added to the composition under pressure at approximately 2-30% preferably 3-20% by volume. The propellant may form a separate layer on the composition or the propellant may be emulsified or miscible in the composition.

The compositions of the invention can be used in any of a variety of applications including use as a sanitizer for application to a surface. The compositions of the invention are suitable for use on mammalian skin including the human hands. In some embodiments, the compositions may be used as a pre-surgical hand scrub. In non-aerosol formulations of the invention, the compositions may be contained in a non-aerosol dispenser equipped with a conventional hand pump, and the composition may be pumped onto the hands or other areas of the body. The pumping action required to dispense the compositions will create a discrete volume of a dispensed composition in the form of a stable foam.

Likewise, in embodiments comprising an aerosol, the aerosol formulation may be dispensed from a pressurized container in a discrete volume of foamed composition. After dispensing, the foam may be spread upon the surface of the skin to sanitize the skin, the hands or the like. While some residue may remain on the skin following evaporation of the alcohol component, the residue can comprise emollients or the like to provide a desired cosmetic effect. Consequently, the compositions of the invention provide a means for sanitizing skin in the form of a foamable composition which does not need to be rinsed from the skin following application of the foam to the area in need of sanitization. Alternatively, undesired residue remaining on the surface can be rinsed off with water, for example.

From the foregoing, it will be appreciated that the present invention also encompasses systems for dispensing the compositions comprising a reservoir and an amount of composition retained therein, and means for dispensing the composition from the reservoir.

The compositions of the present invention may be prepared by a variety of techniques and the ingredients may be added to one another in any order of addition. To ensure a composition of maximum stability, the components may be subjected to high shear (e.g. homogenized) for a limited time period.

EXAMPLES

The following non-limiting Examples are provided to illustrate features of the invention. are not intended to limit the scope of the invention. All percent amounts are weight/weight percent (wt/wt %) unless otherwise noted.

Preparation of Compositions

The compositions in the Examples were prepared in 60 gram samples by combining all components in a glass jar and rolling the jar overnight, on a mechanical roller. The foam builder was introduced to the mixture by first preparing a premix of the foam builder at ranges from 0.5% to 8.0% wt/wt, prepared in water/alcohol. The appropriate weight of premix was then added to the mixture containing the other components prior to the step of mixing by rolling overnight.

According to the Material Safety Data Sheets of certain dimethicone copolyol surfactants, the surfactants are known to contain significant quantities of PEO/PPO block copolymers of the type described herein as builders. These copolymers may be byproducts of the manufacturing process for the copolyol surfactants. The surfactants and builders used in the compositions of the Examples are listed in Tables 1 and 2.

TABLE 1

Surfactants

| Trade Name | INCI Name | Surfactant Mfr. | Mfr. Location |
|---|---|---|---|
| Abil B 8852 | PEG/PPG-4/12 Dimethicone | Goldschmidt Chemical Corp. | Hopewell, VA |
| Abil B 8873 | PEG/PPG-35/65 Dimethicone 7,000 MW | Goldschmidt Chemical Corp. | Hopewell, VA |
| Dow 190 Fluid[1] | PEG/PPG-18/18 Dimethicone | Dow Corning | Midland, MI |
| Dow 193 Fluid[2] | PEG-12 Dimethicone, Hydroxyl terminated | Dow Corning | Midland, MI |
| Lambent MFF-164 | Hydroxyl capped dimethicone copolyol | Lambent Technologies Inc. | Gurnee, IL |
| Lambent Quat AD | Silicone Quaternary 1 | Lambent Technologies Inc. | Gurnee, IL |
| Lambent Quat AM | Silicone Quaternary 2 (Myristyl) | Lambent Technologies Inc. | Gurnee, IL |
| Lambent Syngard 300 | Acrylic backbone polymer with dimethylsiloxane sidechains | Lambent Technologies Inc. | Gurnee, IL |
| Lambent Wax WS-L | Dimethicone copolyol Laurate | Lambent Technologies Inc. | Gurnee, IL |
| Lambent Wax WS-p | Silicone Copolyol Pelargonate | Lambent Technologies Inc. | Gurnee, IL |
| Pecosil DCL | Dimethicone Copolyol Lactate | PCI Pheonix Chemical, Inc. | Somerville, NJ |
| Pecosil DCT | Sodium Dimethicone Copolyol Acetyl Methytaurate | PCI Pheonix Chemical, Inc. | Somerville, NJ |
| Q2-5220 Resin Modifier[3] | PEG/PPG-17/18 Dimethicone | Dow Corning | Midland, MI |

TABLE 1-continued

Surfactants

| Trade Name | INCI Name | Surfactant Mfr. | Mfr. Location |
|---|---|---|---|
| Silwax WD-IS | Silicone Copolyol Isostearate | Lambent Technologies Inc. | Gurnee, IL |
| Silwet 77 | PEG Dimethicone, Methoxy Terminated, 600 MW | GE Silicones | Midland, MI |
| Silwet L-7001 | EO/PO, Methoxy terminated 20,000 MW | GE Silicones | Wilton, CT |
| Silwet L-7200 | Dimethicone Copolyol | GE Silicones | Midland, MI |
| Silwet L-7500 | PPO Dimethicone, Butoxy Terminated, 3,000 MW | GE Silicones | Midland, MI |
| Silwet L-7602 | PEG Dimethicone, Methoxy Terminated, 3000 MW | GE Silicones | Wilton, CT |
| Silwet L-7604 | PEG Dimethicone, Hydroxy Terminated, 4000 MW | GE Silicones | Midland, MI |
| Silwet L-7605 | PEG Dimethicone, Methoxy Terminated, 6000 MW | GE Silicones | Wilton, CT |
| Silwet L-7614 | PEG Dimethicone, Hydroxy Terminated, 5000 MW | GE Silicones | Wilton, CT |
| 3M ™ Silicones "Plus" Polymer VS80 | Polysilicone-8 | 3M Company | St. Paul, MN |

1. Dow 190 surfactant includes poly(ethylene oxide, propylene oxide) monoallyl ether acetate and polyether polyol acetate.
2. Dow 193 surfactant includes polyethylene oxide monoallyl ether.
[3] Q2-5220 Resin Modifier includes poly(ethylene oxide, propylene oxide) monoallyl ether acetate; polyethylene glycol monoallyl ether acetate; and polyether polyol acetate.

TABLE 2

Foam Builders

| Trade Name | Description | Supplier/Mfr. | Mfr. Location |
|---|---|---|---|
| Aqualon EC K100 | Ethylcellulose | Hercules | Wilmington, DE |
| Crothix Liquid | PEG-150 Pentaerythrityl tetrastearate (and) PEG-6 Capric/Caprylic glycerides | Croda | Parsippany, NJ |
| Ecopol 120-S | Hydroxypropyl Guar | Economy Polymers and Chemicals | Houston, TX |
| Ganex P-904LC | Butylated Polyvinyl Pyrrolidone | ISP Technologies | Wayne, NJ |
| Natrosol Plus | Cetyl hydroxyethylcellulose | Hercules | Wilmington, DE |
| Plasdone PVP K-120 | Polyvinyl Pyrrolidone | International Specialty Products | Wayne, NJ |
| Pluronic F-108 | Ethylene Oxide/Propylene Oxide Block Copolymer | BASF | Florham Park, NJ |
| Pluronic F-127 | Ethylene Oxide/Propylene Oxide Block Copolymer | BASF | Florham Park, NJ |
| Polyox WSR N12K | poly(ethylene oxide) Ave MW 1,000,000 | Dow Chemical Co. | Midland, MI |
| Polyox WSR N60K | poly(ethylene oxide) Ave MW 2,000,000 | Dow Chemical Co. | Midland, MI |
| Polyox WSR N-80 | poly(ethylene oxide) Ave MW 200,000 | Dow Chemical Co. | Midland, MI |
| Polyox WSR-301 | poly(ethylene oxide) Ave MW 4,000,000 | Dow Chemical Co. | Midland, MI |
| PVP K-90 | Polyvinyl Pyrrolidone (K value 90) | BASF | Florham Park, NJ |

Equipment

Foam Pump—A foam pump nozzle was used to generate foam from each composition. The pump used was a pump dispenser, product Code F2, type F2-L11 255/150, available from Airspray International Inc. of North Pompano Beach, Fla.

Foam Collection vial—Vials were used to collect foam from the pump dispenser while the foam height was being measured. The vials were made of glass and were of either 40 or 80 mm height having a 25 mm internal diameter and a 27 mm outer diameter.

Test Methods

Foam Height Test Procedure

The Foam Pump was used to assess the foam forming property of the compositions. The pump was rinsed between samples with deionized water by pumping water through the pump until it came out clear. The pump dip tube was removed from the water and then pumped dry of residual water and then placed in the composition to be tested. The pump was then pumped 3 times to prime the pump and then 3 more times to purge solution through the nozzle to ensure the system was ready. Finally, three pumps worth of foam were collected in a collection vial by pumping slowly at a speed of about 1 second for each pump. The vial containing the foam was placed on a flat surface, a timer was started and a small ruler with millimeter increments was used to measure the approximate height of the foam, ignoring the height of any remaining unfoamed composition. The time to measure the foam height usually took about 5 seconds. Any composition producing a foam which was not stable at least 5 seconds was considered unstable and rated 0 mm. The foam height was estimated to be the average height of the foam. A rating of 0 mm was given if the top of the solution was void of foam in any spot, usually the center. The foam height was recorded after 1, 3 and 5 minutes to determine the long term stability of the foam.

Foam Volume % Increase

The percentage of foam volume increase over the solution volume was calculated by measuring the foam height in millimeters, subtracting 5 mm from the foam height and dividing the result by 5 (the volume of the un-foamed pumped solution) and multiplying by 100%. Foam volume % increase measurements were made immediately following creation of the foam (e.g., after dispensing). Due to the difficulty in determining the exact foam surface, foam heights between 0-5 mm were reported as having a zero percent increase in foam volume.

Viscosity

Viscosity in centipoise (cP) was measured at 23° C. at ambient pressure using a Brookfield viscometer Model LVT equipped with a Brookfield LV spindle # 1 @ 60 rpm. All samples were allowed to equilibrate at 23° C. for 24 hours prior to measurement. The viscosity was taken at the lowest speed possible while staying within 10-100% of the viscometer range and more preferably between 20-80% of the range. The viscosity was read after one minute of testing. In all cases the sample size and container geometry was chosen to ensure that there were no wall effects. By "wall effects" it is meant the viscosity value is not affected by the container and is essentially equivalent to the viscosity taken in an infinitely large container. For this reason lower viscosity samples required a larger sample size to accommodate the larger spindles.

Examples 1-13

Examples 1-13 were prepared using various amounts of the surfactant Dow 190; plus a poly(ethylene oxide) (PEO) foam builder, available from Dow Chemical Company of Midland, Mich., under the trade name POLYOX™ WSR N12K; distilled water, and an alcohol solvent. Foam height measurements according to the above test method were taken for each sample. The foam height measurements and formulations for each of the Examples are set forth in Table 3.

TABLE 3

| Example | Dow 190 Surf. Amt. % | Foam BuilderN12K Amt. % | Water Amt. % | SDA[1] (EtOH/IPA) | IPA[2] | Initial Foam Height mm | Foam Height 1 min. mm | Foam Height 3 min. mm | Foam Height 5 min. mm |
|---|---|---|---|---|---|---|---|---|---|
| 1 | 1.00 | 0.060 | 43.94 | 55.00 | — | 32 | 30 | 24 | 23 |
| 2 | 1.00 | 0.060 | 38.94 | 60.00 | — | 32 | 29 | 28 | 22 |
| 3 | 1.00 | 0.060 | 35.17 | 63.77 | — | 35 | 33 | 29 | 20 |
| 4 | 1.00 | 0.060 | 28.94 | 70.00 | — | 34 | 32 | 26 | 18 |
| 5 | 1.00 | 0.060 | 23.94 | 75.00 | — | 28 | 26 | 21 | 17 |
| 6 | 1.00 | 0.060 | 18.94 | 80.00 | — | 30 | 29 | 23 | 14 |
| 7 | 1.00 | 0.060 | 43.94 | — | 55.00 | 36 | 35 | 32 | 28 |
| 8 | 1.00 | 0.060 | 34.94 | — | 64.00 | 35 | 33 | 29 | 23 |
| 9 | 0.50 | 0.060 | 35.44 | — | 64.00 | 25 | 23 | 20 | 14 |
| 10 | 1.00 | 0.060 | 23.94 | — | 75.00 | 17 | 5 | 1 | 0 |
| 11 | 1.00 | 0.060 | 18.94 | 80.00 | — | 35 | 32 | 25 | 16 |
| 12 | 1.00 | 0.060 | 8.94 | 90.00 | — | 27 | 23 | 14 | 8 |
| 13 | 1.00 | 0.060 | 34.94 | 0.00 | 64.00[3] | 26 | 25 | 21 | 14 |

[1] SDA is Specially Denatured Alcohol (SDA-3-C): a mixture of 100 parts USP 200 proof Ethanol plus 5 parts isopropyl alcohol (IPA).
[2] IPA is isopropyl alcohol, reagent grade.
[3] n-propanol (reagent grade) was used instead of isopropyl alcohol.

Examples 14-32

Examples 14-32 were all prepared with the same alcohol solvent, foam builder, surfactant and water content. The only variation in Examples 14-32 was the type of surfactant used. The alcohol solvent was SDA-3-C and was present at 64.00%; the foam builder was PEO N12K (listed above) and was present at 0.06%; the water content was 25.50% and the amount of surfactant was 2.50%. Foam height data and foam volume % increased data are reported in Table 4 for each of the compositions.

TABLE 4

| Example | Surfact. Trade Name | Initial Foam Height mm | Foam Height 1 min. mm | Foam Height 3 min. mm | Foam Height 5 min. Mm | Foam Volume % Increase |
|---|---|---|---|---|---|---|
| 14 | Dow 190 Fluid | 45 | 42 | 28 | 12 | 800% |
| 15 | Dow 193 Fluid | 30 | 0 | 0 | 0 | 500% |
| 16 | Abil B 8873 | 35 | 31 | 25 | 7 | 600% |
| 17 | Lambent MFF-164 | 34 | 32 | 28 | 22 | 580% |
| 18 | Lambent Quat AD | 25 | 7 | 5 | 3 | 400% |
| 19 | Lambent Quat AM | 30 | 0 | 0 | 0 | 500% |
| 20 | Lambent Wax WS-L | 30 | 6 | 0 | 0 | 500% |
| 21 | Lambent Wax WS-p | 35 | 26 | 0 | 0 | 600% |
| 22 | Pecosil DCL | 34 | 20 | 0 | 0 | 580% |
| 23 | Pecosil DCT | 15 | 0 | 0 | 0 | 200% |
| 24 | Q2-5220 Resin Modifier | 30 | 27 | 23 | 14 | 500% |
| 25 | Silwax WD-IS | 10 | 0 | 0 | 0 | 100% |
| 26 | Silwet 77 | 20 | 0 | 0 | 0 | 300% |
| 27 | Silwet L-7001 | 35 | 34 | 29 | 16 | 600% |
| 28 | Silwet L-7500 | 10 | 0 | 0 | 0 | 100% |
| 29 | Silwet L-7602 | 38 | 5 | 0 | 0 | 660% |
| 30 | Silwet L-7604 | 34 | 0 | 0 | 0 | 580% |
| 31 | Silwet L-7605 | 30 | 0 | 0 | 0 | 500% |
| 32 | Silwet L-7614 | 30 | 0 | 0 | 0 | 500% |

Examples 33-53 and Comparative Examples C1-C6

The Examples 33-53 were all prepared with the same alcohol content of 65.00% USP 200 proof ethanol. The amounts and type of surfactant, the amount of foam builder and the water content were varied. Comparative Examples C1-C4 had no surfactant. Examples C5 and C6 had no builder. Formulations, initial foam height measurements and foam volume % increases are reported in Table 5.

TABLE 5

| Example | Surf. Type | Surf. Amt. % | Foam Builder N12K Amt. % | Water Amt. % | Visc. Cp | Initial Foam Height mm | Foam Height 1 min. mm | Foam Height 3 min. mm | Foam Vol. % Increase |
|---|---|---|---|---|---|---|---|---|---|
| C1 | Silwet L-7604 | 0.00 | 0.000 | 35.00 | 3.4 | 0 | 0 | 0 | 0% |
| 33 | Silwet L-7604 | 0.10 | 0.000 | 34.90 | 3.1 | 5 | 0 | 0 | 0% |
| 34 | Silwet L-7604 | 1.00 | 0.000 | 34.00 | 3.5 | 10 | 5 | 1 | 100% |
| C2 | Silwet L-7604 | 0.00 | 0.060 | 34.94 | 3.8 | 0 | 0 | 0 | 0% |
| 35 | Silwet L-7604 | 0.10 | 0.060 | 34.84 | 4.1 | 18 | 0 | 0 | 260% |
| 36 | Silwet L-7604 | 1.00 | 0.060 | 33.94 | 4.0 | 21 | 3 | 0 | 320% |
| 37 | Silwet L-7604 | 5.00 | 0.060 | 29.94 | 3.9 | 17 | 0 | 0 | 240% |
| C3 | Silwet L-7604 | 0.00 | 0.200 | 34.80 | 5.6 | 0 | 0 | 0 | 0% |
| 38 | Silwet L-7604 | 0.10 | 0.200 | 34.70 | 5.5 | 18 | 0 | 0 | 260% |
| 39 | Silwet L-7604 | 1.00 | 0.200 | 33.80 | 4.9 | 23 | 18 | 0 | 360% |
| C4 | Silwet L-7604 | 0.00 | 0.500 | 34.50 | 15.4 | 0 | 0 | 0 | 0% |
| 40 | Silwet L-7604 | 0.10 | 0.500 | 34.40 | 16.5 | 16 | 0 | 0 | 220% |
| 41 | Dow 190 | 1.00 | 0.060 | 33.94 | 3.9 | 40 | 38 | 35 | 700% |
| 42 | Dow 190 | 1.00 | 0.000 | 34.00 | 1.5 | 15 | 9 | 6 | 200% |
| 43 | Lambent AD | 1.00 | 0.060 | 33.94 | 4.0 | 20 | 0 | 0 | 300% |
| C5 | Lambent AD | 1.00 | 0.000 | 34.00 | 3.1 | 0 | 0 | 0 | 0% |
| 44 | Lambent WS-P | 1.00 | 0.060 | 33.94 | 4.1 | 34 | 30 | 8 | 580% |
| 45 | Lambent WS-P | 1.00 | 0.000 | 34.00 | 3.0 | 11 | 8 | 3 | 120% |
| 46 | MFF-164 | 1.00 | 0.060 | 33.94 | 3.0 | 35 | 34 | 32 | 600% |
| 47 | MFF-164 | 1.00 | 0.000 | 34.00 | 2.5 | 14 | 10 | 7 | 180% |

TABLE 5-continued

| Example | Surf. Type | Surf. Amt. % | Foam Builder N12K Amt. % | Water Amt. % | Visc. Cp | Initial Foam Height mm | Foam Height 1 min. mm | Foam Height 3 min. mm | Foam Vol. % Increase |
|---|---|---|---|---|---|---|---|---|---|
| 48 | Pecosil DCT | 1.00 | 0.060 | 33.94 | 3.5 | 10 | 0 | 0 | 100% |
| C6 | Pecosil DCT | 1.00 | 0.000 | 34.00 | 3.0 | 0 | 0 | 0 | 0% |
| 49 | Silwet L-7604 | 1.00 | 0.500 | 33.50 | 16.0 | 17 | 13 | 0 | 240% |
| 50 | Lambent Syngard 300 | 1.00 | 0.060 | 34.94 | nt[1] | 33 | 32 | 30 | 560% |
| 51 | Abil B 8852 | 1.00 | 0.060 | 34.94 | nt | 34 | 34 | 20 | 580% |
| 52 | Silwet L-7200 | 1.00 | 0.060 | 34.94 | nt | 37 | 39 | 32 | 640% |
| 53 | 3M VS80 | 1.00 | 0.060 | 34.94 | nt | 26 | 18 | 14 | 420% |

[1]"nt"—not tested.

Examples 54-64

Examples 54-64 were all prepared with the same alcohol content of 65.00% USP 200 proof ethanol and the same surfactant content of 1.00% Q2-5220 Resin Modifier. The amounts and the type of foam builder were varied as was the water content. Composition, foam height and foam volume % increase are reported in Table 6.

TABLE 6

| Example | Foam Builder Type | Foam Builder Amt. % | Water Amt. % | Visc. Cp | Initial Foam Height mm | Foam Height 1 min. mm | Foam Height 3 min. mm | Foam Height 5 min. Mm | Foam Vol. % Increase |
|---|---|---|---|---|---|---|---|---|---|
| 54 | None | 0.000 | 34.00 | nt[1] | 10 | 9 | 7 | 6 | 100% |
| 55 | Crothix | 0.080 | 33.92 | nt | 12 | 10 | 7 | 7 | 140% |
| 56 | Crothix | 0.300 | 33.70 | 4.9 | 12 | 9 | 8 | 6 | 140% |
| 57 | Ganex P-904LC | 0.080 | 33.92 | nt | 11 | 9 | 8 | 8 | 120% |
| 58 | Ganex P-904LC | 0.300 | 33.70 | 7.4 | 10 | 8 | 8 | 7 | 100% |
| 59 | Pluronic F-108 | 0.080 | 33.92 | nt | 10 | 7 | 6 | 6 | 100% |
| 60 | Pluronic F-108 | 0.300 | 33.70 | 3.1 | 10 | 9 | 7 | 7 | 100% |
| 61 | Pluronic F-127 | 0.080 | 33.92 | nt | 11 | 9 | 7 | 6 | 120% |
| 62 | Pluronic F-127 | 0.300 | 33.70 | 8.6 | 13 | 10 | 9 | 9 | 160% |
| 63 | PVP K-90 | 0.080 | 33.92 | nt | 13 | 10 | 9 | 7 | 160% |
| 64 | PVP K-90 | 0.300 | 33.70 | 4.3 | 9 | 9 | 6 | 6 | 80% |

[1]"nt"—not tested.

Examples 65-73

Examples 65-73 were all prepared with the same surfactant content of 1.00%, Dow 190. The amounts of foam builder, water content and USP 200 proof ethanol were all varied. Additionally the type of foam builder was also varied. Composition, foam height and foam volume % increase are reported in Table 7.

TABLE 7

| Example | Foam Builder Type | Foam Builder Amt. % | Water Amt. % | EtOH Amt. % | Initial Foam Height mm | Foam Height 1 min. mm | Foam Height 3 min. mm | Foam Height 5 min. Mm | Foam Vol. % Increase |
|---|---|---|---|---|---|---|---|---|---|
| 65 | None | 0 | 34.00 | 65.00 | 15 | 13 | 11 | 9 | 200% |
| 66 | Natrosol Plus | 0.06 | 33.98 | 64.96 | 13 | 10 | 8 | 6 | 160% |
| 67 | Natrosol Plus | 0.35 | 33.88 | 64.77 | 6 | 6 | 4 | 4 | 20% |
| 68 | Aqualon EC K100 | 0.06 | 33.98 | 64.96 | 15 | 11 | 10 | 8 | 200% |
| 69 | Aqualon EC K100 | 0.35 | 33.88 | 64.77 | 13 | 10 | 8 | 8 | 160% |
| 70 | Ecopol 120-S | 0.06 | 33.98 | 64.96 | 12 | 9 | 8 | 7 | 140% |
| 71 | Ecopol 120-S | 0.35 | 33.88 | 64.77 | 17 | 15 | 14 | 11 | 240% |
| 72 | PVP K-120 | 0.06 | 33.98 | 64.96 | 14 | 11 | 9 | 8 | 180% |
| 73 | PVP K-120 | 0.35 | 33.88 | 64.77 | 9 | 7 | 6 | 6 | 80% |

Examples 74-78

Examples 74-78 were formulated using PEO builders of different molecular weights. Dow 190 in an amount of 1.00% was used as the surfactant for all of the Examples 68-72. Formulation information and foam height data are given in Table 7. Fluid at an amount of 1.00%.

TABLE 8

| Example | PEO Foam Builder Type | PEO Foam Builder MW | Foam Builder Amt. % | Water Amt. % | Alcohol Solvent Amt. %[1] | Initial Foam Height mm | Foam Height 1 min. mm | Foam Height 3 min. mm | Foam Height 5 min. mm |
|---|---|---|---|---|---|---|---|---|---|
| 74 | WSR-301 | 4,000,000 | 0.060 | 29.94 | 69.00 | 22 | 15 | 10 | 8 |
| 75 | N60K | 2,000,000 | 0.060 | 29.94 | 69.00 | 28 | 24 | 20 | 14 |
| 76 | N12K | 1,000,000 | 0.060 | 29.94 | 69.00 | 26 | 24 | 20 | 16 |
| 77 | WSR N-80 | 200,000 | 0.060 | 34.94 | 64.00 | 14 | 13 | 11 | 9 |
| 78 | none | 0 | 0.0 | 35.00 | 64.00 | 9 | 9 | 8 | 8 |

[1] The alcohol in Examples 68-70 was 190 proof USP ethanol. The alcohol in Examples 71-72 was SDA-3-C alcohol solvent.

Secondary Antimicrobials

Table 9 list various additional (secondary to alcohol) antimicrobials that were added to the formulations described in Examples 73-76.

TABLE 9

| Abbreviated Name | Description | Supplier/Mfr. | Mfr. Location |
|---|---|---|---|
| CHG | 20% Chlorhexidine Gluconate solution | Medichem, S. A, distributed by George Uhe Company, Inc. | Paramus, NJ |
| PCMX | para-chloro-meta-xylenol | Ferro Corporation | Cleveland, OH |
| Triclosan | IRGASAN ® DP 300 | Ciba | Greensboro, NC |
| Citric Acid | Citric Acid | MCB Reagents | Rahway, NJ |
| GML | Glycerol monolaurate | Med-Chem Labs | Galena, IL |
| SCL | Sodium Capril Lactylate | Rita Corp. | Woodstock, IL |

Examples 79-82

Examples 79-82 were formulated with the same components except that different secondary antimicrobials were used, as shown in Table 10. Foam height and foam volume % increase data are also set forth in Table 10.

TABLE 10

| Example | Surf. Dow 190 Amt. % | Foam Builder WSR-N12K Amt. % | Water Amt. % | Alcohol SDA-3-C Amt. % | Secondary Anti-Micro. | Anti-Micro. Amt. % | Initial Foam Height mm | Foam Height 5 min. mm | Foam Vol. % Increase |
|---|---|---|---|---|---|---|---|---|---|
| 79 | 1.00 | 0.060 | 34.17 | 63.77 | CHG | 1.00 | 35 | 15 | 600% |
| 80 | 1.00 | 0.060 | 34.17 | 63.77 | PCMX | 1.00 | 40 | 15 | 700% |
| 81 | 1.00 | 0.060 | 34.17 | 63.77 | Triclosan | 1.00 | 36 | 12 | 620% |
| 82 | 1.00 | 0.060 | 31.97 | 63.77 | GML + CA + SCL[1] | 1.00 | 26 | 2 | 420% |

[1]Glycerol monolaurate at 1.00% + 2.00% citric acid + 0.1% sodium capril lactylate

Examples 83-107

Examples 83-107 were prepared to have the same alcohol content of 69.00% of USP 190 proof ethanol. The Dow 190 surfactant and WSR-301 foam builder were used in various amounts as described in Table 11. Additionally, one or more emollient was added to each of the formulations. Formulations, initial foam height measurements and foam volume % increase are reported in Table 11.

TABLE 11

| Example | Surf. Dow 190 Amt. % | Foam Builder WSR301 Amt. % | Water Amt. % | M1[1] | M2[2] | M3[3] | Initial Foam Height mm | Foam Height 1 min. mm | Foam Height 3 min. mm | Foam Vol. % Increase |
|---|---|---|---|---|---|---|---|---|---|---|
| 83 | 1.00 | 0.06 | 28.94 | 1.00 | 0.00 | 0.00 | 24 | 18 | 14 | 380% |
| 84 | 3.00 | 0.01 | 26.50 | 0.50 | 0.00 | 1.00 | 15 | 12 | 10 | 200% |
| 85 | 2.00 | 0.01 | 26.00 | 1.00 | 1.00 | 1.00 | 17 | 14 | 10 | 240% |
| 86 | 1.00 | 0.06 | 27.94 | 1.00 | 1.00 | 0.00 | 20 | 15 | 10 | 300% |
| 87 | 3.00 | 0.06 | 26.00 | 0.00 | 1.44 | 0.50 | 29 | 25 | 22 | 480% |
| 88 | 1.49 | 0.04 | 26.49 | 0.50 | 2.00 | 0.50 | 30 | 28 | 26 | 500% |
| 89 | 3.00 | 0.04 | 26.00 | 0.00 | 0.97 | 1.00 | 34 | 31 | 24 | 580% |
| 90 | 1.00 | 0.01 | 27.99 | 0.00 | 1.00 | 1.00 | 12 | 9 | 8 | 140% |
| 91 | 1.00 | 0.01 | 27.99 | 1.00 | 0.00 | 1.00 | 14 | 9 | 8 | 180% |
| 92 | 1.00 | 0.01 | 29.00 | 0.50 | 0.50 | 0.00 | 15 | 10 | 8 | 200% |
| 93 | 3.00 | 0.06 | 26.00 | 1.00 | 0.94 | 0.00 | 25 | 20 | 18 | 400% |
| 94 | 1.94 | 0.06 | 26.00 | 1.00 | 2.00 | 0.00 | 30 | 28 | 23 | 500% |
| 95 | 1.00 | 0.06 | 28.94 | 0.00 | 0.00 | 1.00 | 27 | 22 | 16 | 440% |
| 96 | 1.00 | 0.01 | 26.99 | 1.00 | 2.00 | 0.00 | 15 | 11 | 9 | 200% |
| 97 | 1.50 | 0.01 | 29.00 | 0.00 | 0.00 | 0.50 | 15 | 10 | 10 | 200% |
| 98 | 3.00 | 0.01 | 26.00 | 0.00 | 1.99 | 0.00 | 15 | 13 | 9 | 200% |
| 99 | 2.97 | 0.06 | 26.00 | 1.00 | 0.00 | 0.97 | 25 | 23 | 18 | 400% |
| 100 | 3.00 | 0.01 | 26.00 | 0.00 | 1.99 | 0.00 | 16 | 14 | 12 | 220% |
| 101 | 2.00 | 0.06 | 27.94 | 0.00 | 0.00 | 1.00 | 30 | 22 | 17 | 500% |
| 102 | 1.91 | 0.06 | 27.10 | 0.51 | 0.91 | 0.51 | 36 | 31 | 25 | 620% |
| 103 | 1.00 | 0.01 | 26.99 | 0.00 | 2.00 | 1.00 | 14 | 10 | 7 | 180% |
| 104 | 1.00 | 0.06 | 27.94 | 0.00 | 2.00 | 0.00 | 30 | 25 | 21 | 500% |
| 105 | 3.00 | 0.01 | 26.99 | 1.00 | 0.00 | 0.00 | 15 | 12 | 8 | 200% |
| 106 | 1.00 | 0.06 | 26.00 | 0.97 | 1.97 | 1.00 | 31 | 30 | 25 | 520% |
| 107 | 2.00 | 0.06 | 27.94 | 1.00 | 0.00 | 0.00 | 31 | 28 | 20 | 520% |

[1]M1 was Myristyl Alcohol, available from Sasol North America, Westlake, LA.
[2]M2 was G-18-O, glycereth 18 ethylhexanoate, available from Global 7, Franklin, NJ.
[3]M3 was Glycerol, available from from Dow Chemical, Midland MI.

Examples 108-113

Examples 108-113 were prepared with the same alcohol content of 63.77% SDA-3-C; the same amount of surfactant, Dow 190 at 1.00% and the same foam builder PEO, N12K, at an amount of 0.060%, The type and amount emollient was varied, as was the amount of water. Initial foam height measurements and foam volume % increase were taken and are report in Table 12.

TABLE 12

| Example | Water Amt. % | M1[1] | M4[2] | M5[3] | Initial Foam Height mm | Foam Height 1 min. Mm | Foam Height 3 min. mm | Foam Height 5 min. mm | Foam Vol. % Increase |
|---|---|---|---|---|---|---|---|---|---|
| 108 | 34.67 | 0.50 | 0.00 | 0.00 | 38 | 33 | 28 | 18 | 660% |
| 109 | 34.17 | 1.00 | 0.00 | 0.00 | 37 | 34 | 23 | 13 | 640% |
| 110 | 33.17 | 2.00 | 0.00 | 0.00 | 30 | 28 | 24 | 15 | 500% |
| 111 | 32.17 | 3.00 | 0.00 | 0.00 | 30 | 24 | 24 | 15 | 500% |
| 112 | 32.17 | 0.00 | 3.00 | 0.00 | 36 | 35 | 30 | 21 | 620% |
| 113 | 32.17 | 0.00 | 0.00 | 3.00 | 35 | 34 | 26 | 15 | 600% |

[1]M1: Myristyl Alcohol, available from Sasol North America, Westlake, LA.
[2]M4: Triethyl Citrate, NF available from Morflex Inc. of Greensboro, NC.
[3]M5: Acetyl Triethyl Citrate, NF available from Morflex Inc. of Greensboro NC.

TABLE 13

Components for Comparative Examples C7-C16

| Trade/Abbrev. Name | Description | Supplier/Mfr. | Mfr. Location |
|---|---|---|---|
| Monateric CAB-NPB | Cocamido Propyl Betaine | Uniqema | Wilmington, DE |
| BRIJ 52 | PEO 2 cetyl alcohol | Uniqema | Wilmington, DE |
| Silwet L-7200 | Dimethicone Copolyol 19,000 MW 75/25 EO/PO Ratio | GE Silicones | Midland, MI |
| Standamid KD | Cocamide DEA | Kraft Chemical Co. | Melrose Park, IL |
| Super Solen PEG-75 | PEG-75 Lanolin | Croda | Parsippany, NJ |
| Myristyl Alcohol | Myristyl Alcohol | Sasol | Westlake, LA |
| Tween 61 | PEO 4 Sorbitan monostearate | Uniqema | Wilmington, DE |
| Dermal DIA | Diisopropyl Adipate | Alzo International | Sayreville, NJ |
| Cetearyl alcohol | 50:50 wt blend of Cetyl and Stearyl alcohol | Croda | Parsippany, NJ |
| PG | Propylene Glycol | Dow Chemical | Midland, MI |
| Methocel 40-100 | Hydroxypropyl methylcellulose | Dow Chemical | Midland, MI |
| Klucel | Hydroxy Propyl Cellulose | Hercules | Wilmington, DE |
| Ritapro 300 | cetearyl alcohol and ceteareth-20 | Rita Corp. | Woodstock, IL |
| Brij 72 | Steareth-2 | Uniqema | Wilmington, DE |
| Brij 721 | Steareth-21 | Uniqema | Wilmington, DE |
| Polysorbate 80 | Polysorbate 80 | Sigma Chemical Co. | St. Louis, MO |
| PEG 400 | Polyethylene glycol 400 MW | Dow Chemical | Midland, MI |
| Sodium Dodecyl benzene sulfonate | Sodium Dodecyl benzene sulfonate | Pfaltz and Bauer | Waterbury, CT |
| Citric Acid | Citric Acid | MCB Reagents | Rahway, NJ |
| Glycerol monolaurate | Glycerol monolaurate | Med-Chem Labs | Galena, IL |
| Sodium Capril Lactylate | Sodium Capril Lactylate | Rita Corp. | Woodstock, IL |

Comparative Examples C7-C8

Comparative Examples C7 and C8 were tested for initial foam height after being prepared using the materials of Table 13 in the amounts listed in Tables 14A and 14B.

TABLE 14A

| Example | CHG Soln. 20% | Cetearyl alcohol | Tween 61 | PG | USP Ethanol 190 Proof | Water | Initial Foam Height mm |
|---|---|---|---|---|---|---|---|
| C7 | 5.00 | 2.50 | 0.50 | 3.00 | 57.00 | 22.80 | 0 |

TABLE 14B

| Example | Myristyl alcohol | Brij 52 | Glycerol | IPA | Water | Initial Foam Height mm |
|---|---|---|---|---|---|---|
| C8 | 3.00 | 0.80 | 2.50 | 60.00 | 25.40 | 0 |

Comparative Examples C9-C11

Comparative Examples C9, C10 and C11 were prepared using the materials listed in Table 13 in the amounts listed in Table 15 and were tested using the standard Foam Height procedure described above. The Initial Foam Height for each Comparative Example C9-C11, was 0 mm.

TABLE 15

| Ex. # | Silwet L-7200 | Cocamido Propyl Betaine | Kraft Standamid KD | Methocel 40-100 | PEG-75 Lanolin | Glycerin | IPA | USP Ethanol 200 Proof | Water |
|---|---|---|---|---|---|---|---|---|---|
| C9 | 0.20 | 10.00 | 7.00 | 1.00 | 3.00 | 0.20 | — | 60.00 | 17.97 |
| C10 | 0.25 | 10.00 | 7.00 | 1.00 | 3.00 | 0.05 | — | 60.00 | 18.07 |
| C11 | 0.25 | 10.00 | 7.00 | 1.00 | 3.00 | 0.05 | 70.0 | — | 8.07 |

Comparative Examples C12-C14

Comparative Examples C12, C13 and C14 were prepared using various materials of Table 13 in the amounts listed in Table 16 and were tested using the standard Foam Height procedure described above.

TABLE 16

| Ex. # | Ritapro 300 | Brij 72 | Brij 721 | Klucel | USP Ethanol 200 Proof | Water | CHG 20% Soln. | Initial Foam Height mm |
|---|---|---|---|---|---|---|---|---|
| C12 | 2.50 | 1.88 | 0.625 | 0.20 | 60.00 | 14.62 | 0.060 | 0 |
| C13 | 2.50 | 1.88 | 0.625 | 0.20 | 60.00 | 24.71 | 0.200 | 0 |
| C14 | 2.50 | 1.88 | 0.625 | 0.20 | 60.00 | 32.23 | 0.200 | 0 |

Comparative Examples C15-C16

Comparative Examples C15 and C16 were prepared using various materials of Table 13 in the amounts listed in Table 17 and were tested using the standard Foam Height procedure described above.

TABLE 17

| Ex. # | Sodium Dodecyl benzene sulfonate | Polysorbate 80 | Glycerol | PEG 400 | Propylene glycol | USP Ethanol 200 Proof | Water | Initial Foam Height mm |
|---|---|---|---|---|---|---|---|---|
| C15 | 3.00 | 1.00 | 1.50 | 0.50 | 0.00 | 55.00 | 37.25 | 0 |
| C16 | 3.00 | 3.00 | 0.00 | 0.00 | 2.00 | 60.00 | 31.00 | 0 |

Various modifications and alterations of the present invention will be apparent to those skilled in the art without departing from the scope and spirit of the present invention. The Examples described in this application are illustrative of the possibilities of varying the type, quantity and ratio of composition as well as the methods for making formulations of the present invention.

The invention claimed is:
1. A non-aerosol foamable composition, comprising:
  (A) monohydric alcohol present in the composition at a concentration from about 35% to about 99.5% by weight;
  (B) a dimethicone surfactant;
  wherein the dimethicone surfactant is selected from the group consisting of hydroxy-terminated dimethicone copolyol, hydroxyl-capped dimethicone copolyol, methoxy-terminated dimethicone copolyol, butoxy-terminated dimethicone copolyol, silicone copolyol pelargonate, Silicone Quaternary 1, Silicone Quaternary 2 (Myristyl), sodium dimethicone copolyol acetyl methyltaurate, dimethicone bisamino hydroxypropyl copolyol, dimethicone copolyol acetate, dimethicone copolyol adipate, dimethicone copolyol laurate, dimethicone copolyolamine, dimethicone copolyol benzoate, dimethicone copolyol phthalate, dimethicone copolyol undecylenate, dimethicone copolyol crosspolymer, dimethicone copolyol lactate, dimethicone propyl pg-betaine, polysilicone-10, bis-hydroxyethoxypropyl dimethicone, disodium copolyol dimethicone sulfosuccinate, copolyol pg-coco-glucoside dimethicone, copolyol nonafluorohexyl dimethicone copolymer, copolyol methyl ether lauroxy peg amidopropyl dimethicone, sodium carboxydecyl copolyol dimethicone; and combinations of two or more of the foregoing; and
  (C) a polymeric foam builder present in an amount sufficient to provide a stable foam formed from the composition, wherein a stable foam maintains a measurable height for at least 5 seconds following creation of the foam;
  wherein the polymeric foam builder is selected from the group consisting of poly(ethylene oxide) having a molecular weight in the range from about 1,000,000 to 10,000,000, ethyl cellulose, hydroxyethyl cellulose, hydroxypropyl cellulose, cetyl hydroxyethyl cellulose, ethyilhydroxy ethyl cellulose, hydroxypropyl guar, polyglycerol, polyoxamer having a molecular weight of at least 100,000, polyoxamine, polyacrylamide, polyethylene glycol esters and ethers with alkyl alcohols or acid functional alkyls, polyacrylamidomethylpropane sulfonic acid, polyacrylic acid, polyethylene/isopropyl maleate/malaic acid copolyol, polymethacrylamidopropyltrimonium chloride, polymethacrylamidopropyltrimonium methosulfate, polymethacrylic acid, polyquaternium-1 to polyquaternium-9, polyquaternium-11 to polyquaternium-47, polyvinyl methyl ether, butylated polyvinyl pyrrolidone, polyvinyl pyrrolidone, crosslinked and non-crosslinked homopolymer or crosslinked and non-crosslinked copolymer containing n-vinyl lactam monomeric units, and combinations of two or more of the foregoing;

wherein the foamable composition in a pre-foamed state has a viscosity of no greater than about 50 cps at 23° C.

2. The composition of claim 1 which demonstrates a percentage foam volume increase of at least 100%.

3. The composition of claim 1 wherein the viscosity of the composition prior to foaming at 23° C. is within the range from about 0.5 cps to about 50 cps.

4. The composition of claim 1 wherein the foamable composition in a pre-foamed state has a viscosity of no greater than about 20 cps at 23° C.

5. The composition of claim 4 wherein the viscosity of the composition prior to foaming at 23° C. is within the range from about 0.5 cps to about 20 cps.

6. The composition of claim 1 wherein the foam is formed from the foamable composition without the use of a propellant when shaken or dispensed from a dispenser.

7. The composition of claim 1 wherein the foam builder is selected from the group consisting of poly(ethylene oxide) having a molecular weight in to range from about 1,000,000 to 10,000,000, ethyl cellulose, hydroxyothyl cellulose, hydroxypropyl cellulose, hydroxypropyl guar, ethylhydroxy ethyl cellulose, polyoxamer, polyacrylamide, polyethylene glycol esters and ethers with alkyl alcohols or acid functional alkyls, polyacrylic acid, polyquaternium-2, polyquaternium-4, polyquaternium-11, polyquaternium-15, polyquaternium-16, polyquaternium-22, polyquaternium-24, polyquaternium-28, polyquaternium-44, polyquaternium-46, butylated polyvinyl pyrrolidone, polyvinyl pyrrolidone, crosslinked and non-crosslinked homopolymer or crosslinked and non-crosslinked copolymer containing n-vinyl lactam monomeric units, and combinations of two or more of the foregoing.

8. The composition of claim 1 wherein the foam builder is a homopolymer or copolymer containing N-vinyl lactam monomeric units selected from the group consisting of N-vinyl-2-pyrrolidone, N-vinyl-2-valerolactam, N-vinyl-2-caprolactam, and mixtures of any of the foregoing, and optionally one or more comonomers selected from the group consisting of N,N-dimethylacrylamide, acrylic acid, methacrylic acid, hydroxyethylmethacrylate, acrylamide, 2-acrylamido-2-methyl-1-propane sulfonic acid or its salt, vinyl acetate, and mixtures of any of the foregoing.

9. The composition of claim 1 wherein the foam builder is selected from the group consisting of poly(ethylene oxide) having a molecular weight in the range from about 1,000,000 to 10,000,000, polyethylene-polypropylene copolymer, hydroxyethyl cellulose, hydroxypropyl cellulose, and combinations of two or more of the foregoing.

10. The composition of claim 1 wherein the monohydric alcohol is selected from the group consisting of ethanol, propanol, butanol, and combinations of two or more of the foregoing.

11. The composition of claim 1 wherein the monohydric alcohol is present in the composition at a concentration from about 60% to about 80% by weight.

12. The composition of claim 1 wherein the surfactant is present in the composition at a concentration from about 0.1% to about 10% by weight.

13. The composition of claim 12 wherein the surfactant is present in the composition at a concentration from about 0.5% to about 5% by weight.

14. The composition of claim 1 wherein the foam builder is present in the composition at a concentration between about 0.001% and about 5% by weight.

15. The composition of claim 1 wherein the foam builder is present in the composition at a concentration less than or equal to about 0.5% by weight.

16. The composition of claim 15 wherein the foam builder is present in the composition at a concentration less than or equal to about 0.1% by weight.

17. The composition of claim 16 wherein the foam builder is present in the composition at a concentration of about 0.06% by weight.

18. The composition of claim 1 wherein the dimethicone surfactant is selected from hydroxy-terminated dimethicone copolyol, methoxy-terminated dimethicone copolyol, butoxy-terminated dimethicone copolyol, or combination of two or more of the foregoing.

19. The composition of claim 1 further comprising an emollient wherein the emollient is present in the composition at a concentration of about 30% by weight or less.

20. The composition of claim 1 further comprising an antimicrobial agent, present in the composition at a concentration up to about 10% by weight.

21. The composition of claim 1 further comprising one or more skin barrier materials in an amount from about 0.1% to 60% by weight 22. The composition of claim 1 further comprising an antifungal agent.

23. The composition of claim 20 wherein the antimicrobial agent is selected from the group consisting of parachlorometaxylenol, triclosan, chlorhexidine and its salts, polyhexamethylene biguanide and its salts, iodine, idodophors, fatty acid monoesters, poly-n-vinyl pyrrolidone-iodophors, silver oxide, silver and its salts, peroxides, antibiotics, and combinations of two or more of the foregoing.

24. The composition of claim 23 wherein the antimicrobial agent is benzoyl peroxide.

25. The composition of claim 21 wherein the barrier material is selected from the group consisting of aldioxa, allantoin, aluminum acetate, aluminum hydroxide, bismuth subnitrate, boric acid, calamine, cellulose, cholecalciferol, cocoa butter, cod liver oil, colloidal oatmeal, cysteine hydrochloride, dexpanthenol, dimethicone, glycerin kaolin, lanolin, live yeast cell derivative, mineral oil, peruvian balsam, peruvian balsam oil, pertrolatum, protein hydrolysate, racemethionine, shark liver oil, sodium bicarbonate, sulfur, talc, tannic acid, topical starch, vitamin A, white petrolatum, zinc acetate, zinc carbonate, zinc oxide and combinations of two or more of the foregoing.

26. A system comprising:
a dispenser comprising a reservoir and a hand pump; and
the foamable composition of claim 1 contained within the reservoir.

27. A method for sanitizing a surface, comprising:
applying a volume of a non-aerosol foamable composition according to present claim 1 to a surface, which upon shaking or dispensing from a dispenser forms a foam with a percentage foam volume increase of at least 100%, wherein the composition does not include a propellant, and the foam formed maintains a measurable height for at least 5 seconds following creation of the foam.

28. The method of claim 27 wherein the foamable composition in a pre-foamed state has a viscosity of no greater than about 20 cps at 23° C.

29. The method of claim 27 wherein the surface is human skin

30. The method of claim 27 wherein a discrete volume of stable foam is applied to the surface of the skin and subsequently spread out across the surface of the skin.

31. The method as defined in claim 30 further comprising rinsing the surface of the skin with water.

* * * * *

UNITED STATES PATENT AND TRADEMARK OFFICE
CERTIFICATE OF CORRECTION

| | | |
|---|---|---|
| PATENT NO. | : 7,651,990 B2 | Page 1 of 1 |
| APPLICATION NO. | : 11/151563 | |
| DATED | : January 26, 2010 | |
| INVENTOR(S) | : Robert A Asmus | |

It is certified that error appears in the above-identified patent and that said Letters Patent is hereby corrected as shown below:

<u>Title page 2, item (56);</u>
References Cited, under "Other Publications", line 16, delete "Somasurdaran" and insert in place thereof --Somasundaran,--.
References Cited, under "Other Publications", line 19, delete "Formable" and insert in place thereof --Foamable--.

<u>Column 5,</u>
Line 19, delete "concentrations" and insert in place thereof --concentration--.
Line 21, delete "then" and insert in place thereof --than--.

<u>Column 25,</u>
Line 9, delete "report" and insert in place thereof --reported--.

<u>Column 28,</u>
Line 22, after "copolyol" insert --lactate, dimethicone copolyol--.
Lines 22-23, after "adipate" delete "dimethicone copolyol laurate,".
Line 57, delete "ethyilhydroxy" and insert in place thereof --ethylhydroxy--.

<u>Column 29,</u>
Line 25, delete "to" and insert in place thereof --the--.
Line 26, delete "hydroxyothyl" and insert in place thereof --hydroxyethyl--.

<u>Column 30,</u>
Line 63, delete "5seconds" and insert in place thereof --5 seconds--.

Signed and Sealed this
Twenty-sixth Day of July, 2011

David J. Kappos
*Director of the United States Patent and Trademark Office*